United States Patent [19]

Schwendemann et al.

[11] 4,354,979
[45] Oct. 19, 1982

[54] PREPARATION OF ALIPHATIC ISOCYANATES

[75] Inventors: Volker Schwendemann, Wiesenbach; Dietrich Mangold, Neckargemuend, both of Fed. Rep. of Germany

[73] Assignee: BASF Aktiengesellschaft, Ludwigshafen, Fed. Rep. of Germany

[21] Appl. No.: 307,725

[22] Filed: Oct. 2, 1981

[30] Foreign Application Priority Data

Oct. 29, 1980 [DE] Fed. Rep. of Germany ....... 3040692

[51] Int. Cl.$^3$ ............................................ C07C 118/00
[52] U.S. Cl. .................................................. 260/453 P
[58] Field of Search ..................................... 260/453 P

[56] References Cited

U.S. PATENT DOCUMENTS 3,275,669  9/1966  Ulrich et al. ................... 260/453 P
3,372,180  3/1968  Ulrich .............................. 260/455
3,392,184  7/1968  Ulrich et al. ................... 260/453 P

*Primary Examiner*—Dolph H. Torrence
*Attorney, Agent, or Firm*—John H. Shurtleff

[57] ABSTRACT

Organic isocyanates are prepared by thermal decomposition of N,N'-disubstituted allophanic acid esters in an organic carbonate at from 150° to 400° C.

The isocyanates obtainable by this process are valuable starting materials for the preparation of crop protection agents, pesticides, dyes, synthetic resins, plastics, textile waterproofing agents, detergents, bleaching agents and adhesives.

5 Claims, No Drawings

PREPARATION OF ALIPHATIC ISOCYANATES

The present invention relates to a process for the preparation of organic isocyanates by thermal decomposition of N,N'-disubstituted allophanic acid esters in an organic carbonate at from 150° to 400° C.

The preparation of isocyanates by thermal dehydrohalogenation of carbamyl halides is known. The latter compounds, obtainable from amines and phosgene, are cleaved, at an elevated temperature, to the corresponding isocyanates and hydrogen chloride. However, this synthesis principle is virtually restricted to isocyanates with boiling points above the decomposition temperatures of the corresponding carbamyl halides (R. J. Slocombe, J. Amer. Chem. Soc., 72 (1950), 1888–1891.

However, this criterion is not met by the lower isocyanates. In the case of these, when the decomposition temperature of the carbamyl halide is reached, the superheated isocyanate passes into the vapor phase and undergoes an exothermic reaction with hydrogen chloride in the coldest part of the apparatus, thereby reforming the starting material (L. Gattermann, Ann. 244 (1888), 35).

The preparation of isocyanates by thermal decomposition of carbamic acid esters or ureas is also known (Houben-Weyl, Methoden der Organischen Chemie, Volume 8 (1952), page 126).

Ureas which lend themselves to pyrolysis are trisubstituted ureas containing at most two aryl groups (German Pat. No. 748,714), with the proviso that the two amide groups of the ureas employed correspond to two amines of substantially different boiling point.

The thermal decomposition of carbamic acid esters is advantageously carried out with aryl carbamates, which can be cleaved to the isocyanate and the hydroxyl component under milder conditions than the alkyl carbamates. Furthermore, isocyanates react substantially more rapidly with aliphatic hydroxyl components to give carbamates than with the corresponding aromatic hydroxy compounds.

A disadvantage in all these processes is the high consumption of phosgene, an extremely toxic compound which requires considerable safety precautions. In all these processes, at least one mole of phosgene is consumed per mole of isocyanate to be formed, even if the reaction is stoichiometric.

Several processes seek to circumvent this disadvantage by using, as the starting compound for the preparation of the alkyl isocyanate, an N,N'-disubstituted urea which is very easily obtainable from carbon dioxide and the corresponding amine.

Thus, according to U.S. Pat. No. 3,275,669, the allophanic acid chlorides obtainable from phosgene and N,N'-dialkylureas can be converted, preferably in the presence of acid acceptors, into two moles of isocyanate. However, in the case of the lower alkyl isocyanates, the same problems arise as have already been described in connection with the preparation of the isocyanates from the carbamyl halides. Furthermore, the use of bases results in increased polymerization of the base-sensitive isocyanates.

U.S. Pat. Nos. 3,372,180 and 3,392,184 describe processes for the preparation of 2,4-disubstituted allophanic acid esters, and the thermal decomposition of the latter into isocyanates and hydroxy compounds. This reaction however gives satisfactory yields only if the compound pyrolyzed is an aryl N,N'-dialkylallophanate, of which the ester moiety corresponds to a high-boiling phenol. Even on passing from 2,6-di-t-butyl-4-methylphenyl N,N'-dimethyl-allophanate (boiling point of 2,6-di-t-butyl-4-methylphenol: 265° C.) to 3-t-butylphenyl N,N'-dimethyl-allophanate (boiling point of 3-t-butylphenol: 240° C.), the yield of methyl isocyanate drops by about 20%. On going to phenyl N,N'-dimethyl-allophanate (boiling point of phenol: 182° C.), the isocyanate yield decreases yet further (Comparative Example 5).

We have found that aliphatic isocyanates of the formula $$R^1\text{-NCO} \qquad \text{I}$$

where $R^1$ is an aliphatic radical, are obtained in an advantageous manner by thermal cleavage if an N,N'-disubstituted allophanic acid ester of the formula

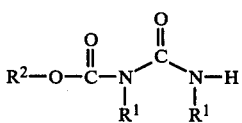

where the $R^1$'s may be identical or different and have the above meanings and $R^2$ is an aromatic radical derived from an unsubstituted or substituted phenol which is distillable at below 250° C. is thermally cleaved at from 150° to 400° C. in the presence of a diester of carbonic acid, of the formula

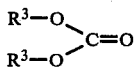

where the $R^3$'s may be identical or different and each is an aliphatic, cycloaliphatic, araliphatic or aromatic radical, or the $R^3$'s together are an unsubstituted or substituted alkylene or phenylene radical.

As an example, if phenyl N,N' dimethylallophanate is used, in diphenyl carbonate as the reaction medium, the reaction can be represented by the following equation:

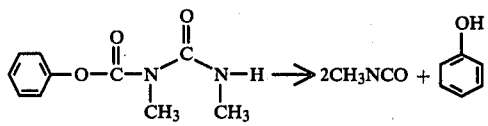

Compared to the conventional process, the process according to the invention surprisingly gives a large number of aliphatic isocyanates more simply and more economically, in substantially better yield, better space-time yield and greater purity, and in particular does so when operated on an industrial scale and by a continuous method. All these advantageous results are surprising since, in view of the presence of the highly reactive compound III, the various possible ways in which the starting material II can react, and the higher temperature used, a mixture of numerous components, and a lower yield and lower purity of the end product I would have been expected. Compared to U.S. Pat. Nos. 3,275,669, 3,372,180 and 3,392,184, the high yield when using compound III is surprising.

Preferred starting materials II and compounds III and accordingly preferred end products I are those where the $R^1$'s can be identical or different and each is alkyl of 1 to 7 carbon atoms or alkenyl of 2 to 7 carbon atoms, and $R^2$ is phenyl which is unsubstituted or substituted by a plurality of or, advantageously, 1 or 2 fluorine or chlorine atoms, o-nitro groups or alkyl or alkoxy groups each of 1 to 4 carbon atoms, with the proviso that the corresponding phenol is distillable below 250° C., and $R^3$ is alkyl of 1 to 7 carbon atoms, alkenyl of 2 to 7 carbon atoms, aralkyl or alkylaryl, each of 7 to 12 carbon atoms, or phenyl, or the 2 $R^3$'s together constitute unsubstituted or substituted alkylene of 2 to 6 carbon atoms or unsubstituted or substituted phenylene of 6 to 12 carbon atoms. The above radicals can be substituted by groups which are inert under the reaction conditions, for example nitro or alkyl or alkoxy, each of 1 to 4 carbon atoms.

Accordingly, suitable starting materials II include phenyl N,N'-dimethylallophanate; the homologous N,N'-diethyl, N,N'-dipropyl, N,N'-diisopropyl, N,N'-dibutyl, N,N'-diisobutyl, N,N'-di-tert.-butyl, N,N'-di-sec.-butyl and N-methyl,N'ethyl derivatives; and the derivatives which are similarly substituted at the two nitrogen atoms and are monosubstituted in the 2-, 3- or 4-position of the phenyl moiety, or disubstituted in the 2',6'-, 2',3'-, 2',4'-, 2',5'-, 3',5'- or 4',5'-position of the phenyl moiety, by methyl, ethyl, propyl, isopropyl, butyl, isobutyl, tert.-butyl, sec.-butyl, allyl, nitro, methoxy, ethoxy, propoxy, fluorine or chlorine, the substituents, in the case of disubstitution, being identical or different.

Examples of suitable starting materials III are diallyl, dibutyl, di-N-butyl, diisobutyl, di-tert.-butyl, di-sec.-butyl, dicyclohexyl, dibenzyl, and diphenyl carbonate, and cyclic carbonates such as ethylene, 1,2-propylene, 1,3-propylene, 1,4-butylene, 1,2-butylene, isobutylene, o-phenylene and m-phenylene carbonate. Preferred starting materials III are those boiling above 150° C., in particular diphenyl, di-α-naphthyl, di-p-nitrophenyl, di-n-decyl, di-o-cresyl, di-m-cresyl and di-p-cresyl carbonate.

Starting material III can be employed in stoichiometric amount, in excess relative to starting material II or in less than the stoichiometric amount; preferably, from 0.01 to 10, especially from 0.1 to 5, moles of starting material II are employed per mole of starting material III. The reaction is in general carried out at from 150° to 400° C., preferably from 180° to 360° C., under reduced pressure, superatmospheric pressure or atmospheric pressure, preferably under atmospheric pressure or reduced pressure, especially at from 200 to 1,000 mbar, batchwise or continuously.

Specifically, the reaction can be carried out as follows: a mixture of starting material II and starting material III is kept at the reaction temperature for from 0.1 to 2 hours. During this time the end product isolated from the reaction mixture in a conventional manner, for example by distillation.

Advantages of the process are the neutral reaction conditions and the absence of catalysts, the fact that no salt is produced and the non-pollution of the environment, since the only products formed in addition to the isocyanates according to the invention are phenols which can be quantitatively re-used for the prepration of the allophanates. Compared to the prior art processes for the preparation of isocyanates, the process according to the invention achieves a substantial reduction in phosgene consumption.

The isocyanates obtainable by the process of the invention are valuable starting materials for the preparation of crop protection agents, pesticides, dyes, synthetic resins, plastics, textile waterproofing agents, detergents, bleaching agents and adhesives. Their conversion to urethanes, for example for use as foams or as high molecular weight, highly flexible, coatings, or to ureas, are of importance. Concerning their use, reference may be made to the above publications and to Ullmanns Encyklopädie der technischen Chemie, Volume 9, pages 11, 12 and 404, and Volume 17, page 204.

In the examples, parts are by weight.

EXAMPLE 1

700 parts of phenyl N,N'-dimethylallophanate and 500 parts of di-p-nitrophenyl carbonate are heated at 240° C. for 90 minutes. The methyl isocyanate formed during the reaction is taken off at the top of a column, and the phenol at the bottom. 376 parts of methyl isocyanate (98% of theory), of boiling point 39°–41° C., are obtained.

EXAMPLE 2

700 parts of phenyl N,N'-dimethylallophanate and 500 parts by weight of di-α-naphthyl carbonate are heated at 225° C. for 90 minutes. The methyl isocyanate formed in the reaction is taken off at the top of a column and the phenol at the bottom. 361 parts of methyl isocyanate (97.1% of theory), of boiling point 39°–41° C., are obtained.

EXAMPLE 3

104 parts of phenyl N,N'-dimethylallophanate and 100 parts of di-n-decyl carbonate are heated at 240° C. for 90 minutes. The methyl isocyanate formed in the reaction is taken off at the top of a column and the phenol at the bottom. 55 parts of methyl isocyanate (96.5% of theory), of boiling point 39°–41° C., are obtained.

EXAMPLE 4

70 parts of phenyl N,N'-dimethylallophanate and 80 parts of diphenyl carbonate are heated at 240° C. in an oil bath for 90 minutes. The methyl isocyanate formed in the reaction is taken off at the top of a column and the phenol at the bottom. 35 parts of methyl isocyanate (91% of theory), of boiling point 39°–41° C., are obtained.

EXAMPLE 5 (COMPARATIVE EXAMPLE)

70 parts of phenyl N,N'-dimethylallophanate are heated at 240° C. in an oil bath for 90 minutes. The methyl isocyanate formed in the reaction is taken off at the top of a column and the phenol at the bottom. 17.9 parts of methyl isocyanate (45.6% of theory), of boiling point 39°–41° C., are obtained.

EXAMPLE 6

47 parts of phenyl N,N'-diethylallophanate and 80 parts of diphenyl carbonate are heated at 240° C. in an oil bath for 90 minutes. The ethyl isocyanate (boiling point 60° C.) formed in the reaction is taken off at the top of a column and the phenol at the bottom. 26.2 parts of ethyl isocyanate (94.6% of theory), of boiling point 60° C., are obtained.

EXAMPLE 7 (COMPARATIVE EXAMPLE)

50 parts of N,N'-diethylallophanate are heated at 240° C. in an oil bath for 90 minutes. The ethyl isocyanate formed in the reaction is taken off at the top of a column and the phenol at the bottom. 15.3 parts of ethyl isocyanate (50.3% of theory), of boiling point 60° C., are obtained.

EXAMPLE 8

51 parts of phenyl N,N'-di-n-propylallophanate and 70 parts of diphenyl carbonate are heated at 240° C. for 90 minutes. The n-propyl isocyanate formed in the reaction is taken off at the top of a column and the phenol at the bottom. 31.7 parts of n-propyl isocyanate (98.5% of theory), of boiling point 88° C., are obtained.

EXAMPLE 9

50 parts of 3-t-butyl-phenyl N,N'-dimethylallophanate and 83 parts of diphenyl carbonate are heated at 240° C. in an oil bath for 90 minutes. The methyl isocyanate formed in the reaction is taken off at the top of a column and the 3-t-butyl-phenol at the bottom. 20.6 parts of methyl isocyanate (95% of theory), of boiling point 39°–41° C., are obtained.

We claim:

1. A process for the preparation of an aliphatic isocyanate of the formula $$R^1\text{-NCO} \qquad \text{I}$$

where $R^1$ is an aliphatic radical, by thermal cleavage, wherein an N,N'-disubstituted allophanic acid ester of the formula

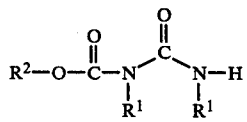

where the $R^1$ may be identical or different and have the above meanings and $R^2$ is an aromatic radical derived from an unsubstituted or substituted phenol which is distillable at below 250° C. is thermally cleaved at from 150° to 400° C. in the presence of a diester of carbonic acid, of the formula

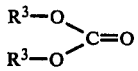

where the $R^3$'s may be identical or different and each is an aliphatic, cycloaliphatic, araliphatic or aromatic radical, or the $R^3$'s together are an unsubstituted or substituted alkylene or phenylene radical.

2. A process as claimed in claim 1, wherein the reaction is carried out with from 0.01 to 10 moles of starting material II per mole of starting material III.

3. A process as claimed in claim 1, wherein the reaction is carried out at from 180° to 360° C.

4. A process as claimed in claim 1, wherein the reaction is carried out under a pressure of from 200 to 1,000 mbar.

5. A process as claimed in claim 1, 2, 3 or 4 wherein said thermal cleavage is carried out with an N,N'-disubstituted allophanic acid ester of the formula

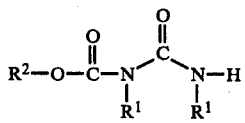

where the $R^1$'s may be identical or different and each is alkyl of 1 to 7 carbon atoms or alkenyl of 2 to 7 carbon atoms, and $R^2$ is phenyl which is unsubstituted or substituted by 1 to 2 fluorine or chlorine atoms, o-nitro groups or alkyl or alkoxy groups each of 1 to 4 carbon atoms, with the proviso that the corresponding phenol is distillable below 250° C., in the presence of a diester of carbonic acid of the formula

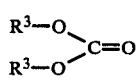

where the $R^3$'s may be identical or different and each is alkyl of 1 to 7 carbon atoms, alkenyl of 2 to 7 carbon atoms, aralkyl or alkylaryl, each of 7 to 12 carbon atoms, or phenyl, or the 2 $R^3$'s together constitute unsubstituted or substituted alkylene of 2 to 6 carbon atoms or unsubstituted or substituted phenylene of 6 to 12 carbon atoms, wherein the above radicals $R^1$, $R^2$ and $R^3$ can be substituted by nitro or by alkyl or alkoxy, each of 1 to 4 carbon atoms.

* * * * *